United States Patent [19]

Hallmann

[11] 3,981,492
[45] Sept. 21, 1976

[54] X-RAY TABLE PATIENT TRANSFER DEVICE OR THE LIKE WITH BODY HOLDING DEVICE

[76] Inventor: David R. Hallmann, 288 Nayatt Road, Barrington, R.I. 02806

[22] Filed: Aug. 4, 1975

[21] Appl. No.: 601,545

[52] U.S. Cl. .............................................. 269/328
[51] Int. Cl.² ........................................ A61G 13/00
[58] Field of Search ........................ 269/322–328, 269/275; 250/439, 445, 446, 447

[56] References Cited
UNITED STATES PATENTS

| | | | |
|---|---|---|---|
| 1,968,120 | 7/1934 | Barghavsen et al.................. | 269/328 |
| 2,241,028 | 5/1941 | Chubb................................. | 269/275 |
| 2,460,679 | 1/1949 | Clay................................... | 269/240 |
| 2,743,974 | 5/1956 | Black................................. | 269/328 |
| 2,787,506 | 4/1957 | Travisano........................... | 269/328 |
| 3,293,667 | 12/1966 | Ohrberg.............................. | 269/323 |
| 3,329,423 | 7/1967 | Kleinman............................ | 269/324 |
| 3,358,141 | 12/1967 | Hoffmann et al................... | 269/328 |
| 3,449,008 | 6/1969 | Colechia............................. | 269/275 |
| 3,779,540 | 12/1973 | Boudreau............................ | 269/328 |

FOREIGN PATENTS OR APPLICATIONS

| | | | |
|---|---|---|---|
| 334,264 | 1/1959 | Switzerland........................ | 269/322 |

Primary Examiner—Al Lawrence Smith
Assistant Examiner—Robert C. Watson
Attorney, Agent, or Firm—Barlow & Barlow

[57] ABSTRACT

An X-ray table, patient transfer device stretcher or the like having rigid opposite side rails with detachable strap attaching means adjustable along opposite side rails with flexible straps extending toward each other from opposite sides in overlapping relation with a means such as filamentary hooks to hold the straps in overlapping relation.

2 Claims, 4 Drawing Figures

U.S. Patent   Sept. 21, 1976   3,981,492
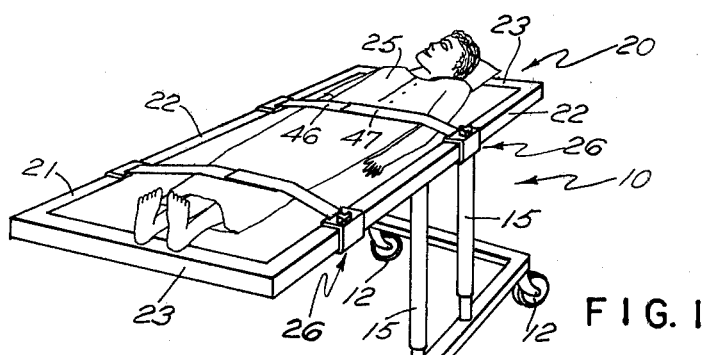
FIG. 1
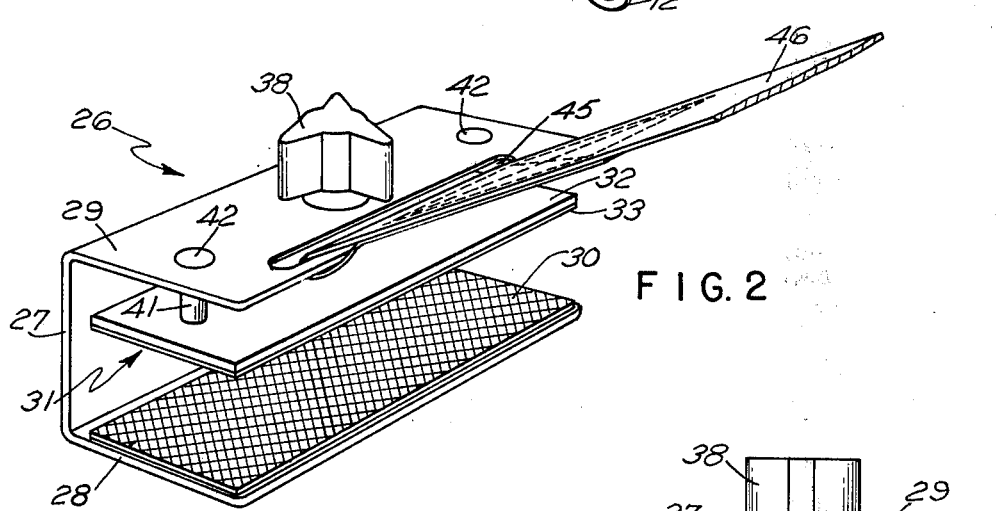
FIG. 2
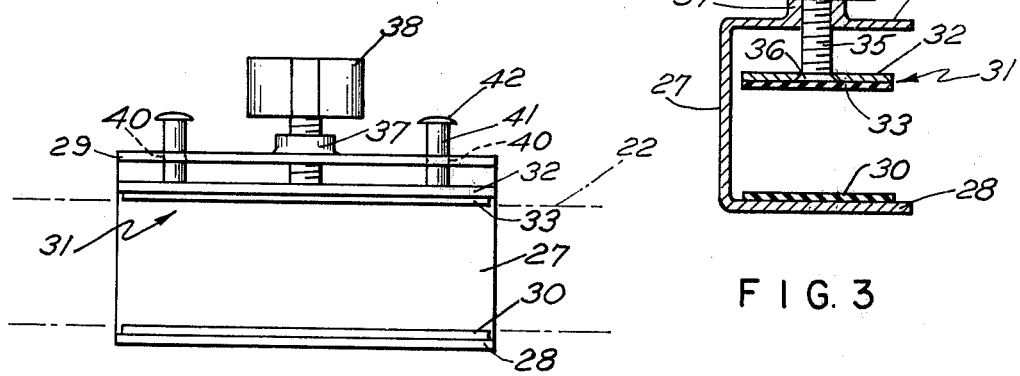
FIG. 3
FIG. 4

X-RAY TABLE PATIENT TRANSFER DEVICE OR THE LIKE WITH BODY HOLDING DEVICE

BACKGROUND OF THE INVENTION

Many X-ray tables or chairs on which a patient lies prone or sitting have no means for holding the patient on the table or chair. In some cases, especially constructed tables are provided with holding means, the special construction being such that it is expensive to produce and in some cases difficult to operate. An illustration of these specially constructed tables may be found in U.S. Pat. Nos. 3,700,229 and 3,358,141 or 2,787,506.

An object of this invention is to provide a simple attachment for an X-ray table or device as above which may be inexpensively formed and easily attached to opposite sides of the device and adjustable along the device so that the straps may be positioned in a location which will not interfere with the X-ray picture to be taken or study to be performed.

SUMMARY OF THE INVENTION

The X-ray table or device as above comprises a generally flat horizontal or vertical supporting means having rigid opposite side rails or frames. Clamps are positioned along the rigid opposite side rails or frames by being in a form to embrace a portion of the rail or frame and secured thereto by hand-operated means with an arrangement for easily securing a body strap to the clamp for extension over the body of the person on the horizontal or vertical supporting means. The straps are equipped with textile material known as Velcro which has hooks and loops so as to be readily attached together or easily detached. When attached, the straps will extend over a part of the body so that the patient cannot get up or fall from the table or chair.

BRIEF DESCRIPTION OF THE DRAWINGS

FIG. 1 is a perspective view showing an X-ray table with a patient thereon and the straps of this invention extending across the body of the patient;

FIG. 2 is a perspective view of the strap attaching means and illustrating a fragmental portion of the strap extending therefrom;

FIG. 3 is a section through the attaching device of FIG. 2; and

FIG. 4 is a section or edge view looking into the open side of the attaching device.

DESCRIPTION OF THE PREFERRED EMBODIMENT

In FIG. 1 I have shown an X-ray table designated generally 10 having a base 11 supported on caster wheels 12 at four locations on the base so that the same may be easily moved about from one place to another. Standards 15 are of a telescoping type so that they may be adjusted vertically, and these standards support a table designated generally 20 and comprising a generally flat horizontally extending mid portion 21 with side rails 22 and end rails 23 which are usually wood but may be of any material suitable for the purpose.

The holding means for the body of the person 25 on the table comprises two flexible straps, one attached to one side and the other attached to the other side of the table by a suitable attaching device such as a clamp 26 having a back portion 27 from which extend at generally right angles thereto the bottom arm 28 and the top arm 29. The bottom arm 28 comprises a lower jaw designed to engage the undersurface of a rail 22 and is provided with a non-skid lining 30 which may be of rubber or some synthetic material, plastic or the like, with a roughened surface so that it may resiliently grip and not slide easily along the rail 22. A movable or second jaw 31 comprises a flat plate 32 which also has an anti-skid lining of rubber or plastic material 33 along its undersurface as shown in FIG. 3. A threaded member 35 is swivelly mounted as at 36 to this plate 32 and extends through a collar 37 mounted on the upper arm 29 of the attaching device. This member 35 is equipped with a handle 38 for turning the same so as to move the jaw 31 toward and from the lower jaw or arm 28. In order to guide this jaw in its movement, openings 40 are provided in the upper arm 29 at either side of the location of the collar 37 and pins 41 having heads 42 are secured to the plate 32 so as to move with the plate toward and from the upper arm 29 and lower arm 28.

The upper arm 29 is provided with a slot 45 and a wide fabric strap 46 extends through this slot and is doubled back on itself and sewed in a loop so as to attach it to the arm 29 of the device.

There are two of these straps 46 and 47, one of which overlaps the other, and on the underside of the upper overlapping strap and on the top side of the under strap there will be provided a hook and loop textile material made in accordance with U.S. Pat. No. 2,717,437 and known as Velcro, so that the straps may be secured in any desired overlapping relation and thus will accommodate bodies such as 25 of various sizes. The straps will be fairly snugly applied to the body and over the arms of the patient 25 so that he is practically immovable and cannot easily roll from the table or get up therefrom to cause a hazard to himself and a problem to the attendants.

It will be apparent from the foregoing that the clamping device with straps can also be used on stretchers and other tables on which patients must be restrained. The device when used in multiple makes it possible to immobilize the proximal portion of an extremity while tension is placed on a distal extremity during radiographic procedures such as Arthrography.

I claim:

1. In an X-ray table or the like, the combination of a relatively flat horizontal body support means having rigid opposite side rails, clamps on said opposite rails, flexible straps secured to each clamp and extending from one side rail toward the other side rail, said straps being of a length to be in overlapping relation, means on said overlapping straps to secure them together in overlapping relation, said clamps comprising a pair of jaws, means to move said jaws toward each other to grip a side rail in a desired location along the side rail and releasable for adjustment along the side rail and re-gripping the rail, each of said clamps comprising a back to be disposed generally vertically when engaging said rail, a lower arm and an upper arm extending at generally right angles to the back, one of said arms serving as a gripping jaw and a second jaw movably mounted on the inner side of the other arm and means to move the second jaw toward and from the first said jaw, the last said means comprising a threaded collar on the said other arm and a threaded member extending through said collar and swivelly attached to said second jaw, each of said upper arms having a slot to receive said strap.

2. The subject matter of claim 1 with guiding means on either side of said collar to direct the second clamping jaw in a path of movement toward and from the first said jaw.

* * * * *